(12) United States Patent  (10) Patent No.: US 7,977,350 B2
Carson et al.  (45) Date of Patent: Jul. 12, 2011

(54) CCR1 ANTAGONISTS AND METHODS OF USE THEREFOR

(75) Inventors: Kenneth G. Carson, Princeton, NJ (US); Geraldine C. B. Harriman, Brookline, MA (US); Shomir Ghosh, Brookline, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/765,070

(22) Filed: Apr. 22, 2010

(65) Prior Publication Data

US 2010/0249174 A1  Sep. 30, 2010

Related U.S. Application Data

(63) Continuation of application No. 11/900,744, filed on Sep. 13, 2007, now Pat. No. 7,732,459.

(51) Int. Cl.
A61K 31/4353 (2006.01)
C07D 491/044 (2006.01)
A61P 29/00 (2006.01)
A61P 9/10 (2006.01)
A61P 3/10 (2006.01)
A61P 17/06 (2006.01)
A61P 37/00 (2006.01)
A61P 37/08 (2006.01)
A61P 37/06 (2006.01)

(52) U.S. Cl. .......................................... 514/291; 546/89
(58) Field of Classification Search .................. 546/89; 514/291

See application file for complete search history.

(56) References Cited

U.S. PATENT DOCUMENTS

| | | | |
|---|---|---|---|
| 3,409,621 A | 11/1968 | Villani et al. |
| 3,770,729 A | 11/1973 | Nakanishi et al. |
| 4,042,695 A | 8/1977 | Buss |
| 4,250,176 A | 2/1981 | Vandenberk et al. |
| 4,335,122 A | 6/1982 | McFadden et al. |
| 4,547,496 A | 10/1985 | Kumazawa et al. |
| 4,567,178 A | 1/1986 | Eberlein et al. |
| 4,645,758 A | 2/1987 | Willman et al. |
| 4,994,463 A | 2/1991 | Oshima et al. |
| 4,999,363 A | 3/1991 | Oshima et al. |
| 5,010,087 A | 4/1991 | Oshima et al. |
| 5,010,104 A | 4/1991 | Oshima et al. |
| 5,011,836 A | 4/1991 | Eberlein et al. |
| 5,089,496 A | 2/1992 | Piwinski et al. |
| 5,116,863 A | 5/1992 | Ohshima et al. |
| 5,118,701 A | 6/1992 | Oshima et al. |
| 5,143,922 A | 9/1992 | Oshima et al. |
| 5,239,083 A | 8/1993 | Kumazawa et al. |
| 5,242,931 A | 9/1993 | Oshima et al. |
| 5,302,596 A | 4/1994 | Oshima et al. |
| 5,302,602 A | 4/1994 | Oshima et al. |
| 5,340,807 A | 8/1994 | Kumazawa et al. |
| 5,378,701 A | 1/1995 | Ohshima et al. |
| 5,478,835 A | 12/1995 | Kumazawa et al. |
| 5,478,840 A | 12/1995 | Ohshima et al. |
| 5,538,986 A | 7/1996 | Ting et al. |
| 5,607,955 A | 3/1997 | Ohshima et al. |
| 5,672,611 A | 9/1997 | Doll et al. |

(Continued)

FOREIGN PATENT DOCUMENTS

CH  421 138  3/1967

(Continued)

OTHER PUBLICATIONS

Davis, M. A., et al., "New Psychotropic Agents.VIII Analogs of Amitriptyline Containing Normeperidine Group," *J. Med. Chem.*, 10:627-635 (1967).

(Continued)

*Primary Examiner* — D. Margaret Seaman
*Assistant Examiner* — Niloofar Rahmani
(74) *Attorney, Agent, or Firm* — McDermott Will & Emery LLP

(57) ABSTRACT

The invention provides compounds having the formula:

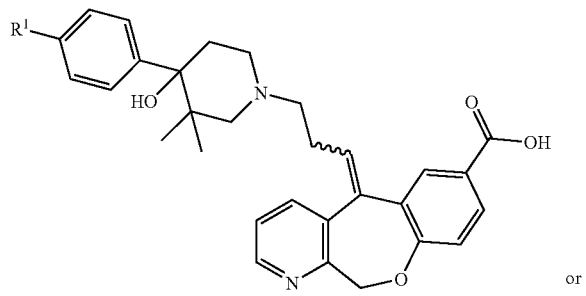

or

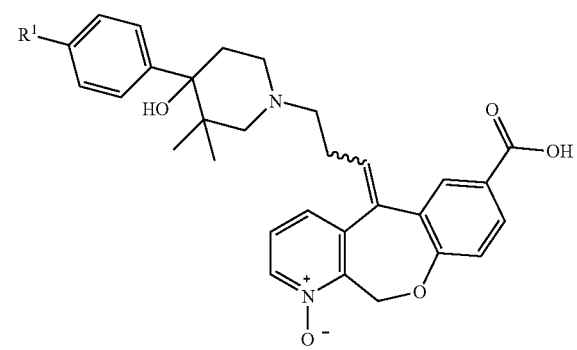

wherein $R^1$ is halogen. The invention also provides compositions comprising the compounds, and methods of treating diseases or disorders that comprise administering one or more of the compounds to a subject in need thereof. The disclosed compounds have CCR1 antagonist activity.

16 Claims, No Drawings

U.S. PATENT DOCUMENTS

| | | | |
|---|---|---|---|
| 5,679,703 | A | 10/1997 | Yanase et al. |
| 5,688,788 | A | 11/1997 | Andersen et al. |
| 5,801,175 | A | 9/1998 | Afonso et al. |
| 5,874,428 | A | 2/1999 | Dorwald |
| 5,877,177 | A | 3/1999 | Taveras |
| 5,919,776 | A | 7/1999 | Hagmann |
| 6,040,318 | A | 3/2000 | Andersen et al. |
| 6,048,856 | A | 4/2000 | Jørgensen et al. |
| 6,150,355 | A | 11/2000 | Kumazawa et al. |
| 6,281,212 | B1 | 8/2001 | Schwender et al. |
| 6,288,083 | B1 | 9/2001 | Luly et al. |
| 6,288,084 | B1 | 9/2001 | Luly et al. |
| 6,323,206 | B1 | 11/2001 | Schwender et al. |
| 6,329,385 | B1 | 12/2001 | Luly et al. |
| 6,433,165 | B1 | 8/2002 | Luly et al. |
| 6,503,926 | B2 | 1/2003 | Luly et al. |
| 6,509,346 | B2 | 1/2003 | Luly et al. |
| 6,613,905 | B1 * | 9/2003 | Luly et al. ............ 546/196 |
| 2002/0169155 | A1 | 11/2002 | Luly et al. |
| 2003/0045516 | A1 | 3/2003 | Luly et al. |
| 2005/0070549 | A1 | 3/2005 | Luly et al. |

FOREIGN PATENT DOCUMENTS

| | | |
|---|---|---|
| CS | 236549 | 5/1985 |
| CS | 236550 | 5/1985 |
| CZ | 240 698 | 6/1987 |
| DE | 80449 | 9/1969 |
| DE | 1 918 739 | 10/1969 |
| DE | 33 26 641 A1 | 2/1984 |
| EA | A1-2000 00693 | 7/1999 |
| EP | 0 235 796 A2 | 9/1987 |
| EP | 0 270 692 A1 | 6/1988 |
| EP | 0 325 755 A1 | 2/1989 |
| EP | 0 309 422 A2 | 3/1989 |
| EP | 0 341 860 A1 | 11/1989 |
| EP | 0 515 158 A1 | 11/1992 |
| EP | 0 524 784 A1 | 1/1993 |
| EP | 0 916 668 A1 | 5/1999 |
| GB | 1 003 292 | 9/1965 |
| GB | 1 003 950 | 9/1965 |
| GB | 1 013 574 | 12/1965 |
| GB | 1 085 406 | 10/1967 |
| GB | 1109847 | 4/1968 |
| GB | 1 206 216 | 9/1970 |
| GB | 1213172 | 11/1970 |
| GB | 1 330 966 | 9/1973 |
| GB | 1 347 935 | 2/1974 |
| JP | 61 167663 | 7/1986 |
| JP | 9-40662 | 2/1997 |
| WO | WO 89/10369 | 11/1989 |
| WO | WO 92/16226 | 10/1992 |
| WO | WO 92/20681 | 11/1992 |
| WO | WO 93/02081 | 2/1993 |
| WO | WO 96/31469 | 10/1996 |
| WO | WO 96/31470 | 10/1996 |
| WO | WO 96/31477 | 10/1996 |
| WO | WO 96/31498 | 10/1996 |
| WO | WO 97/24325 | 7/1997 |
| WO | WO 97/44329 | 11/1997 |
| WO | WO 98/02151 | 1/1998 |
| WO | WO 98/04554 | 2/1998 |
| WO | WO 98/11092 | 3/1998 |
| WO | WO 98/11093 | 3/1998 |
| WO | WO 98/11096 | 3/1998 |
| WO | WO 98/11097 | 3/1998 |
| WO | WO 98/11098 | 3/1998 |
| WO | WO 98/11099 | 3/1998 |
| WO | WO 98/11106 | 3/1998 |
| WO | WO 98/15546 | 4/1998 |
| WO | WO 98/25604 | 6/1998 |
| WO | WO 98/25605 | 6/1998 |
| WO | WO 98/25617 | 6/1998 |
| WO | WO 98/27815 | 7/1998 |
| WO | WO 98/43638 | 10/1998 |
| WO | WO 98/46587 | 10/1998 |
| WO | WO 99/37617 | 7/1999 |
| WO | WO 99/37619 | 7/1999 |
| WO | WO 99/37651 | 7/1999 |
| WO | WO 00/14086 | 3/2000 |
| WO | WO 00/14089 | 3/2000 |
| WO | WO 00/32193 A1 | 6/2000 |
| WO | WO 01/09094 A2 | 2/2001 |
| WO | WO 01/09119 A2 | 2/2001 |
| WO | WO 01/09137 | 2/2001 |
| WO | WO 01/09138 | 2/2001 |
| WO | WO 03/045942 | 6/2003 |

OTHER PUBLICATIONS

Helwig, H., et al., "Helwig/Otto Arzneimittal, Ein Handbuch fur Arzte and Apotheker", pp. 4-1 through 4-24, 8th Ed., (1992).

Sindelar, Karel, et al., "Potential Antidiarrheal Agents: 1-(11-Cyano-6,11-Dihydrodibenzo[b,e]Thiepin-11yl-Alklyl)- and 1-(10-cyano-10,11-Dihydrodibenzo[b,f]Thiepin-10-YL-Alkyl)-4-Substituted Piperidines," *Collection Czechoslovak Chem. Commun.* 50:1089-1096 (1985).

Sindelar, K., et al., Chemical Abstracts, 121:35275n (1994).

Sindelar, Karel, et al., "Antihistamine Substances: Tricyclic Analogues of N-(4,4-Diphenyl-3Butene-1YL)Nipecotic Acid and Some Related Compounds," *Collection Czechoslovak Chem. Commun.* 59:667-674 (1994).

Ali, Fadia E., et al., "Orally Active and Potent Inhibitors of γ-Aminobutyric Acid Uptake," *J. Med. Chem.* 28:653-660 (1985).

Sindelar, Karel, et al., "Potential Antihistaminics: Tricyclic Carboxylic Acids Derived from 6,11-Dihydrodibenzo[b,e]Thiepine and 4,9-Dihydrothieno[2,3-c]-2-Benzothiepine," *Collection Czechoslovak Chem. Commun.* 56:2482-2493 (1991).

Polivka, Zdenek, et al., "Heterocyclic Ethers Derived from 6,11-Dihydrodibenzo-[b,e]Thiepin-11-ols and 4,9-Dihydrothieno[2,3-c]-2-Benzothiepin-4-ol; A New Series of Potential Antidepressants and Antihistamine Agents," *Collection Czechoslovak Chem. Commun.* 51:2034-2049 (1986).

Polivka, Zdenek, et al., "Antiaminic Agents Derived from Thieno[2,3-c]-2-Benzothiepin: 4-(1-Methyl-4-Piperidylidene)-4,9-Dihydrothieno[2,3-c]-2-Benzothiepin and some Related Compounds," *Collection Czechoslovak Chem. Commun.* 48:623-641 (1983).

Rajsner, M., et al., "Neurotropic and Psychotropic Compounds. XXXI Chemistry and Pharmacology of 11-(3-Dimethylaminopropylidene)-2-Mehtyl-6,11-Dihydrodibenzo[b,e] Thiepin and of Some Analogues," *Collection Czechoslovak Chem. Commun.* 34:1015-1024 (1969).

Rajsner, M., et al., "Neurotrope and Psychotrope Substanzen XV. 4,9-Dihydrothieno[2,3-b]Benzo[e]Thiepin-Derivate," *Collection Czechoslovak Chem. Commun.* 32:2854-2866 (1967).

Hesselgesser, Joseph, et al., "Identification and Characterization of Small Molecule Functional Antagonists of the CCR1 Chemokine Receptor", *The Journal of Biological Chemistry*, 273(25):15687-15692 (1998).

Masaru, E. et al., Chemical Abstracts, 93(19), 186323f (1980).
Tsujikawa, T. et al., Chemical Abstracts, 77(25), 164662h (1972).
Nakanishi, M. et al. Chemical Abstracts, 81:25566Z (1974).
Ting, P.C. et al., Chemical Abstracts, 123:227838 (1995).
Kumazawa, T. et al., Chemical Abstracts, 126:212158 (1997).
Kato, K. et al., Chemical Abstracts, 130:237480 (1999).
Davis, M.A. et al., Chemical Abstracts, 67:99959 (1967).
Kukla, Michael J., Chemical Abstracts, 92:198282 (1980).
Protiva, M. et al., Chemical Abstracts, 72:3387 (1970).
Protiva, M. et al., Chemical Abstracts, 109:92794 (1988).
Protiva, M. et al., Chemical Abstracts, 104:19527 (1986).
Protiva, M. et al., Chemical Abstracts, 107:134327 (1987).
Sindelar, K. et al., Chemical Abstracts, 104:33990 (1986).
Michaels, R.J. et al., Chemical Abstracts, 77:88537 (1972).
Foldeak, S. et al., Chemical Abstracts, 105:172012 (1986).
Iorio, L.C. et al., Chemical Abstracts, 115:126879 (1991).
Aftab, D.T. et al., Chemical Abstracts, 116:120373 (1992).

King, Frank D., "Bioisosteres, Conformational Restriction, and Prodrugs-Case History: An Example of a Conformational Restriction Approach," *Medicinal Chemistry: Principles and Practice*, The Royal Society of Chemistry, London, 1995, Chapter 14, pp. 206-208.

Foldeak, S. et al., "The Mannich Reaction of 9-Acteyl- and 9, 10-Dihydro-9-Acetylanthracene. Reduction of the Mannich Bases, and Stereochemistry of the 9, 10-Dihydro Compounds," *Tetrahedron*, 41(24):5913-5918 (1985).

Iorio, L.C. et al., "Anticholinergic Drugs Potentiate Dopamine D1 but not D2 Antagonists on a Conditioned Avoidance Task in Rats," *J. Pharmacol. Exp. Ther.*, 258(1), 118-123 (1991).

Aftab, D.T,. et al., "Structure-Activity Relationships of Phenothiazines and Related Drugs for Inhibition of Protein Kinase C," *Mol. Pharmacol.* 40(5):798-805 (1991).

S.J. Rappaport, Ed., "Inflammation and Phagocytosis," in: *Pysiological Basis of Medical Practice, Twelfth Edition*, J.B. West, Eds., Williams & Wilkins, Baltimore, pp. 362-368 (1990).

Schmelz, M. and Petersen, L.J., "Neurogenic Inflammation in Human and Rodent Skin," *News Physiol. Sci.*, 16:33-37 (2001).

Howard, O.M.Z,. et al., "Chemokines: Progress Toward Identifying Molecular Targets for Therapeutic Agents," TIBTECH., 14:46-51 (1996).

Protiva, M., et al., *Chemical Abstracts*, 107:134326 (1987).

Oshima, E., et al., *Chemical Abstracts*, 115:256025 (1991).

Rovin, et al., "Lymphocytes Induce Monocyte Chemoattractant Protein-1 Production by Renal Cells After Fcγ Receptor Cross-Linking: Role of IL-1β," *Journal of Leukocyte biology*, 69:435-439 (2001).

Pesce, G., et al., "Preliminary Evidence for 'Aberrant' Expression of the Leukocyte Integrin LFA-1 (CD11a/CD18) on Conjunctival Epithelial Cells of Patients with Mite Allergy," *Int. Arch, Allergy Immunol.*, 125:160-163 (2001).

Kishimoto, T. K., et al., "Leukocyte Adhesion Deficiency," *J. Biol. Chem.*, 264(6):3588-3595 (1989).

Cutolo, et al., *Journal of Cellular Biochemistry*, (Aug. 21-Sep. 5, 2001); 83(3):390-400.

* cited by examiner

CCR1 ANTAGONISTS AND METHODS OF USE THEREFOR

RELATED APPLICATION

This application is a continuation of U.S. patent application Ser. No. 11/900,744, filed on Sep. 13, 2007, now U.S. Pat. No. 7,732,459 which claims the benefit of U.S. patent application Ser. No. 11/204,930, filed Aug. 16, 2005, which is a continuation of U.S. patent application Ser. No. 10/706,835, filed Nov. 12, 2003, which claims the benefit of U.S. Provisional Application No. 60/425,947, filed Nov. 13, 2002. The entire teachings of the above applications are incorporated herein by reference.

BACKGROUND OF THE INVENTION

Chemoattractant cytokines or chemokines are a family of proinflammatory mediators that promote recruitment and activation of multiple lineages of leukocytes, such as T lymphocytes. Chemokines can be released by many kinds of tissue cells after activation. Release of chemokines at sites of inflammation mediates the ongoing migration of effector cells during chronic inflammation. The chemokines are related in primary structure and contain four conserved cysteines, which form disulfide bonds. The chemokine family includes the C—X—C chemokines (α-chemokines), and the C—C chemokines (β-chemokines), in which the first two conserved cysteines are separated by an intervening residue, or are adjacent, respectively (Baggiolini, M. and Dahinden, C. A., *Immunology Today,* 15:127-133 (1994)).

The chemokine receptors are members of a superfamily of G protein-coupled receptors (GPCR) which share structural features that reflect a common mechanism of action of signal transduction (Gerard, C. and Gerard, N. P., *Annu Rev. Immunol.,* 12:775-808 (1994); Gerard, C. and Gerard, N. P., *Curr. Opin. Immunol.,* 6:140-145 (1994)). Conserved features include seven hydrophobic domains spanning the plasma membrane, which are connected by hydrophilic extracellular and intracellular loops. The majority of the primary sequence homology occurs in the hydrophobic transmembrane regions with the hydrophilic regions being more diverse. The first receptor for the C—C chemokines that was cloned and expressed binds the chemokines MIP-1α and RANTES. Accordingly, this MIP-1α/RANTES receptor was designated C—C chemokine receptor 1 (also referred to as CCR-1 or CKR-1; Neote, K., et al., *Cell,* 72:415-425 (1993); Horuk, R et al., WO 94/11504, May 26, 1994; Gao, J.-I. et al., *J. Exp. Med.,* 177:1421-1427 (1993)). CCR1 also binds the chemokines CCL2 (MCP-1) CCL4 (MIP-1β), CCL7 (MCP-3), CCL8 (MCP-2), CCL13 (MCP-4), CCL14 (HCC-1), CCL15 (Lkn-1), CCL23 (MPIF-1). (Murphy P. M. et al., International Union of Pharmacology. XXII. Nomenclature for Chemokine Receptors, *Pharmacol. Reviews,* 52:145-176 (2000).) The ability of chemokines, such as RANTES and MIP-1α, to induce the directed migration of monocytes and a memory population of circulating T-cells indicate that chemokines and chemokine receptors may play a critical role in chronic inflammatory diseases, since these diseases are characterized by destructive infiltrates of T cells and monocytes. (See, e.g., Schall, T. et al., *Nature,* 347:669-71 (1990).)

Small molecule antagonists of the interaction between C—C chemokine receptors (e.g., CCR1) and their ligands, including RANTES and MIP-1α, would provide compounds useful for inhibiting pathogenic processes "triggered" by receptor ligand interaction.

SUMMARY OF THE INVENTION

The invention relates to compounds having the formula:

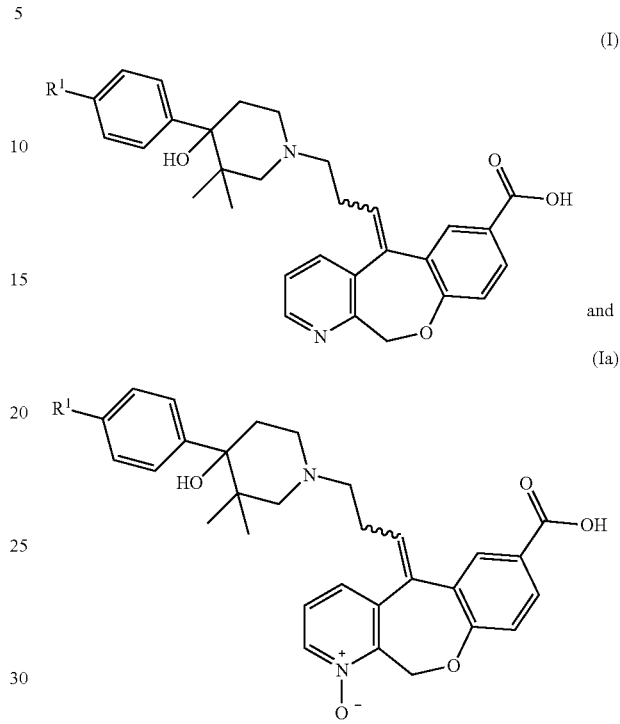

or a physiologically acceptable salt thereof, wherein $R^1$ is halogen.

The invention further relates to a method for treating a disease characterized by pathogenic leukocyte recruitment, pathogenic leukocyte activation or pathogenic leukocyte recruitment and activation. The method comprises administering to a subject in need thereof an effective amount of a compound described herein.

The invention further relates to compositions comprising a compound as described herein and a pharmaceutically or physiologically acceptable carrier or excipient.

The invention further relates to the use of the compounds described herein in therapy (including palliative, curative and prophylactic therapy) or diagnosis, and to the use of such compounds for the manufacture of a medicament for the treatment of a particular disease or condition as described herein (e.g., inflammatory arthritis (e.g., rheumatoid arthritis), inflammatory demyelinating disease (e.g., multiple sclerosis)).

DETAILED DESCRIPTION OF THE INVENTION

The invention relates to compounds that are antagonists of C—C Chemokine Receptor 1 (CCR1), compositions comprising the compounds and methods of treating diseases or disorders that comprise administering one or more of the compounds. The antagonist compounds can inhibit binding of a ligand (e.g., a chemokine ligand such as CCL2 (MCP-1) CCL3 (MIP-1α), CCL4 (MIP-1β), CCL5 (RANTES), CCL7 (MCP-3), CCL8 (MCP-2), CCL13 (MCP-4), CCL14 (HCC-1), CCL15 (Lkn-1), CCL23 (MPIF-1)) to CCR1. Accordingly, processes or cellular responses mediated by the binding of a chemokine to CCR1 can be inhibited (reduced or prevented, in whole or in part), including leukocyte migration, integrin activation, transient increases in the concentration of intracellular free calcium [Ca$^{++}$]$_i$, and/or granule release of proinflammatory mediators.

The compounds have the formula:

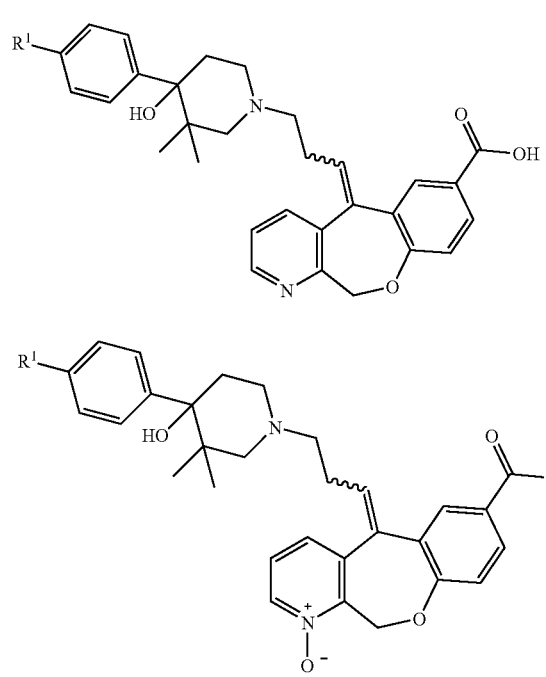

or a physiologically acceptable salt thereof, wherein R$^1$ is a halogen. Preferably, the halogen is selected from the group consisting of chloro, bromo and fluoro. More preferably, the halogen is chloro.

As described herein, compounds of Formula (I) and Formula (Ia) can be prepared as racemates or as substantially pure enantiomers (>99% enantiomeric excess). The optical configuration of the compounds of Formula (I) and Formula (Ia) are assigned using the (R),(S) method of Cahn-Ingold-Prelog. (See, J. March, "Advanced Organic Chemistry," 4$^{th}$ Edition, Wiley Interscience, New York, pp. 109-111 (1992).)

In preferred embodiments, the compound of Formula (I) is the (S)-enantiomer, and has the structure:

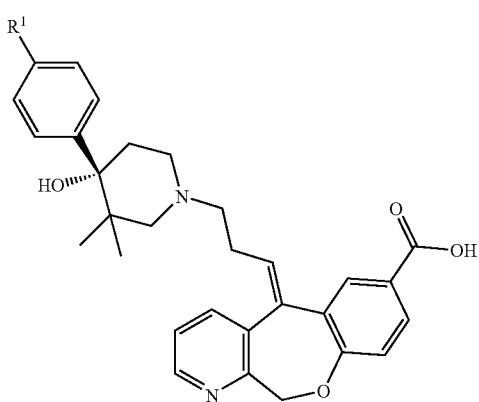

or a physiologically acceptable salt thereof, wherein R$^1$ is a halogen.

In a particularly preferred embodiment, the compound is of Formula II wherein R$^1$ is chloro.

In other preferred embodiments, the compound of Formula (Ia) is the (S)-enantiomer, and has the structure:

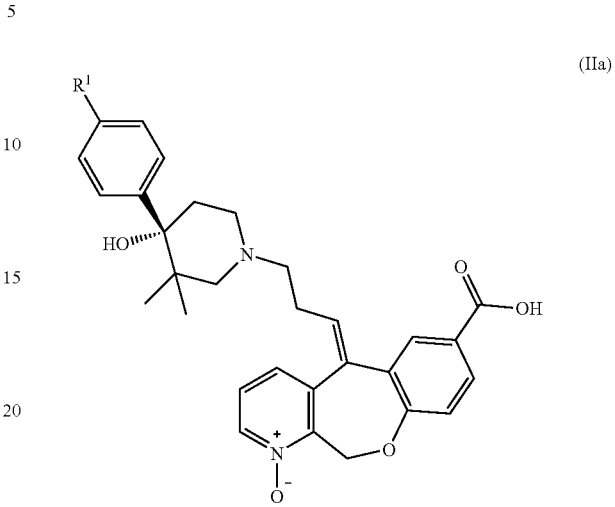

or a physiologically acceptable salt thereof, wherein R$^1$ is a halogen.

In a particularly preferred embodiment, the compound is of Formula IIa wherein R$^1$ is chloro.

The (S)- and (R)-enantiomers of the invention can be prepared using any suitable method. For example, the enantiomers can be resolved from the racemate using chiral chromatography or recrystallization. Preferably, the (S)- and/or (R)-enantiomers are prepared by stereospecific synthesis as described herein.

In accordance with conventional methods for showing structural formulas of compounds, a terminal methyl group in a compound described herein can be shown as a straight line with or without "CH$_3$" on its terminus:

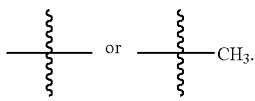

The compounds disclosed herein can be obtained as E- and Z-configurational isomers. It is expressly pointed out that the invention includes compounds of the E-configuration and the Z-configuration around the double bond connecting the tricyclic moiety to the remainder of the molecule, and a method of treating a subject with compounds of the E-configuration, the Z-configuration, and mixtures thereof. Accordingly, in the structural formulas presented herein, the symbol: " ∿ " represents both the E-configuration and the Z-configuration. One configuration can have greater activity than another. Preferably, the pyridyl ring and the piperidinyl ring are in the cis configuration as shown in Formula (II) and Formula (IIa).

The invention includes all isomeric forms and racemic mixtures of the disclosed compounds, and a method of treating a subject with both pure isomers and mixtures thereof, including racemic mixtures.

The compounds described herein can be prepared and administered as neutral compounds, salts, esters, amides and/or prodrugs. As used herein, "pharmaceutically or physiologically acceptable salts, esters, amides, and prodrugs" are those salts (e.g., carboxylate salts, amino acid addition salts), esters, amides, and prodrugs of the compounds of the present invention which are suitable for use in contact with the tissues of a subject without undue toxicity, irritation, allergic response, and the like, commensurate with a reasonable benefit/risk ratio, and effective for their intended use, as well as the zwitterionic forms, where possible, of the compounds of the invention.

Pharmaceutically or physiologically acceptable acid addition salts of the compounds described herein include salts derived from nontoxic inorganic acids such as hydrochloric, nitric, phosphoric, sulfuric, hydrobromic, hydroiodic, hydrofluoric, phosphorous, and the like, and salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, and the like. Such acid additional salts include, for example, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate and methanesulfonate salts. Also contemplated are salts of amino acids such as arginate, gluconate, galacturonate and the like. (See, for example, Berge S. M. et al., "Pharmaceutical Salts," *J. Pharma. Sci.*, 66:1 (1977).)

Acid addition salts of compounds which contain a basic group (e.g., amine) can be prepared using suitable methods. For example, acid addition salts can be prepared by contacting the free base form of a compound with a sufficient amount of a desired acid to produce the salt in the conventional manner. The free base form can be regenerated by contacting the salt form with a base and isolating the free base in the conventional manner. The free base form of a compound can differ from a salt forms somewhat in certain physical properties such as solubility in polar solvents.

Pharmaceutically or physiologically acceptable base addition salts can be formed with suitable metals or amines, such as alkali and alkaline earth metals or organic amines. Examples of metals which are suitable for use as cations in base addition salts include sodium, potassium, magnesium, calcium and the like. Amines suitable for use as cations in base addition salts include N,N'-dibenzylethylenediamine, chloroprocaine, choline, diethanolamine, dicyclohexylamine, ethylenediamine, N-methylglucamine, and procaine. (See, for example, Berge S. M. et al., "Pharmaceutical Salts," *J. Pharma. Sci.*, 66:1 (1977).)

Base addition salts of compounds which contain an acidic group (e.g., carboxylic acid) can be prepared using suitable methods. For example, the free acid form of a compound can be contacted with a sufficient amount of the desired base to produce a salt in the conventional manner. The free acid form can be regenerated by contacting the salt form with a suitable acid and isolating the free acid in the conventional manner. The free acid form of a compound can differ from the base addition salt form somewhat in certain physical properties such as solubility in polar solvents.

The term "prodrug" refers to compounds that can be transformed in vivo (e.g., following administration to an animal), by metabolic processes or other processes, to yield a compound of the above formulae, for example, by hydrolysis in blood. A thorough discussion is provided in T. Higuchi and V. Stella, "Pro-drugs as Novel Delivery Systems," Vol. 14 of the A.C.S. Symposium Series; and *Bioreversible Carriers in Drug Design*, ed. Edward B. Roche, American Pharmaceutical Association and Pergamon Press, 1987, both of which are incorporated herein by reference. Suitable prodrugs include pharmaceutically or physiologically acceptable esters and amides of the compounds described herein. Examples of pharmaceutically or physiologically acceptable, esters of the compounds of this invention include $C_1$-$C_6$ alkyl esters. In certain embodiments, the alkyl group of the alkyl ester is a straight or branched chain $C_1$-$C_6$ alkyl group. Acceptable alkyl esters also include $C_5$-$C_7$ cycloalkyl esters as well as arylalkyl esters such as, but not limited to benzyl. $C_1$-$C_4$ esters are preferred. Esters of the compounds of the present invention can be prepared using any suitable method.

Examples of pharmaceutically or physiologically acceptable, amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$-$C_3$ alkyl primary amines, and $C_1$-$C_2$ dialkyl secondary amines are preferred. Amides of the compounds of the invention may be prepared using any suitable method.

Compositions

The invention also relates to pharmaceutical and/or physiological compositions which contain one or more of the compounds described herein. Such compositions can be formulated for administration by any desired route, such as orally, topically, by inhalation (e.g., intrabronchial, intranasal, oral inhalation or intranasal drops), rectally, transdermally, or parenterally. Generally the compositions comprise a compound of the invention (i.e., one or more compounds) as the active ingredient and a (one or more) suitable carrier, diluent, excipient, adjuvant and/or preservative. Formulation of a compound to be administered will vary according to the route of administration selected (e.g., solution, emulsion, capsule). Standard pharmaceutical formulation techniques can be employed. (See, generally, "Remington's Pharmaceutical Science," 18th Edition, Mack Publishing. (1990); Baker, et al., "Controlled Release of Biological Active Agents," John Wiley and Sons (1986), the entire teachings of both of the foregoing are incorporated herein by reference.)

The presence of microorganisms in the compositions can be controlled by various antibacterial and/or antifungal agents, for example, parabens, chlorobutanol, alcohols (e.g., phenol, benzyl alcohol), sorbic acid, and the like. It may also be desirable to include isotonic agents, for example sugars, sodium chloride, and the like.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, excipients or vehicles include physiological saline, phosphate-buffered saline, Hank's solution, Ringer's-lactate and the like, ethanol, polyols (propyleneglycol, polyethyleneglycol, glycerol, and the like), vegetable oils (such as olive oil) and injectable organic esters such as ethyl oleate, or any suitable mixture thereof. Fluidity can be adjusted, for example, by the use of a coating such as lecithin, by the maintenance of the required particle size in the case of dispersions and by the use of surfactants. When prolonged absorption of an injectable pharmaceutical composition is desired, agents that delay absorption, for example, aluminum monostearate and gelatin can be included.

Solid dosage forms for oral administration include, for example, capsules, tablets, pills, powders, and granules. In such solid dosage forms, the active ingredient (i.e., one or more compounds of the invention) can be admixed with one or more carrier or excipient such as sodium citrate or dicalcium phosphate; (a) fillers or extenders, for example, starches, lactose, sucrose, glucose, mannitol, silicic acid, polyethyleneglycols, and the like; (b) binders, for example, carboxymethylcellulose, alignates, gelatin, polyvinylpyrrolidone, sucrose, and acacia; (c) humectants, for example, glycerol; (d) disintegrating agents, for example, agar-agar, calcium carbonate, potato or tapioca starch, alginic acid, certain complex silicates, and sodium carbonate; (e) solution retarders, for example paraffin; (f) absorption accelerators, for example, quaternary ammonium compounds; (g) wetting agents, for example, cetyl alcohol, and glycerol monostearate; (h) adsorbents, for example, kaolin and bentonite; and (i) lubricants, for example, talc, calcium stearate, magnesium stearate, solid polyethylene glycols, sodium lauryl sulfate, or mixtures thereof. Solid compositions, such as those for oral administration, can also comprise buffering agents. Such solid compositions or solid compositions that are similar to those described can be provided in soft- or hard-filled gelatin capsules if desired.

Solid dosage forms such as tablets, dragées, capsules, pills, and granules can be prepared with coatings and shells, such as enteric coatings or other suitable coatings or shells. Several such coating and/or shells are well known in the art, and can contain opacifying agents, and can also be of such composition that they release the active compound or compounds in a certain part of the intestinal tract in a delayed manner. Examples of embedding compositions which can be used are polymeric substances and waxes. The active compounds can also be used in microencapsulated form, if appropriate, with, for example, one or more of the above-mentioned carriers or excipients.

Liquid dosage forms for oral administration include pharmaceutically acceptable emulsions, solutions, suspensions, syrups, and elixirs. In addition to the active compounds, the liquid dosage forms can contain a suitable carrier or excipient, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like. If desired, the composition can also include wetting agents, emulsifying agents, suspending agents, sweetening, flavoring and/or perfuming agents. Suspensions can contain suspending agents, such as, ethoxylated isostearyl alcohols, polyoxyethylene sorbitol and sorbitan esters, microcrystalline cellulose, aluminum metahydroxide, bentonite, agar-agar, tragacanth, and the like. Mixtures of suspending agents can be employed if desired. Suppositories (e.g., for rectal or vaginal administration) can be prepared by mixing one or more compounds of the invention with suitable nonirritating excipients or carriers such as cocoa butter, polyethyleneglycol, or a suppository wax which is solid at room temperature but liquid at body temperature and melts in the rectum or vagina, thereby releasing the active ingredient.

Dosage forms for topical administration include ointments, powders, sprays and inhalants. The active ingredient can be admixed under suitable conditions (e.g., sterile conditions) with a physiologically acceptable carrier and any preservatives, buffers, or propellants as may be required. Ophthalmic formulations, eye ointments, powders, and solutions can also be prepared, for example, using suitable carriers or excipients. For inhalation, the compound can be solubilized and loaded into a suitable dispenser for administration (e.g., an atomizer, nebulizer or pressurized aerosol dispenser).

The quantity of active ingredient (one or more compounds of the invention) in the composition can range from about 0.1% to about 99.9% by weight. Preferably the quantity of active ingredient is about 10% to about 90%, or about 20% to about 80% by weight. A unit dose preparation can contain from 1 mg to about 1000 mg active ingredient, preferably about 10 mg to about 100 mg active ingredient. The composition can, if desired, also contain other compatible therapeutic agents, such as theophylline, ÿ-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNβ-1b)) and the like.

In one embodiment, the composition comprises (S)-5-{3-[4-(4-Chloro-phenyl)-4-hydroxy-3,3-dimethyl-piperidin-1-yl]-propylidene}-5,11-dihydro-10-oxa-1-aza-dibenzo[a,d]cycloheptene-7-carboxylic acid and a physiologically acceptable carrier or excipient. In another embodiment, the composition is substantially free of (R)-5-{3-[4-(4-Chloro-phenyl)-4-hydroxy-3,3-dimethyl-piperidin-1-yl]-propylidene}-5,11-dihydro-10-oxa-1-aza-dibenzo[a,d]cycloheptene-7-carboxylic acid (contains at least about 98% or at least about 99% enantiomeric excess of (S)-5-{3-[4-(4-Chloro-phenyl)-4-hydroxy-3,3-dimethyl-piperidin-1-yl]-propylidene}-5,11-dihydro-10-oxa-1-aza-dibenzo[a,d]cycloheptene-7-carboxylic acid).

In another embodiment, the composition comprises (S)-5-{3-[4-(4-Chloro-phenyl)-4-hydroxy-3,3-dimethyl-piperidin-1-yl]-propylidene}-5,11-dihydro-10-oxa-1-aza-dibenzo[a, d]cycloheptene-7-carboxylic acid, (R)-5-{3-[4-(4-Chloro-phenyl)-4-hydroxy-3,3-dimethyl-piperidin-1-yl]-propylidene}-5,11-dihydro-10-oxa-1-aza-dibenzo[a,d]cycloheptene-7-carboxylic acid and a physiologically acceptable carrier or excipient. In one embodiment, the composition comprises racemic-5-{3-[4-(4-Chloro-phenyl)-4-hydroxy-3,3-dimethyl-piperidin-1-yl]-propylidene}-5,11-dihydro-10-oxa-1-aza-dibenzo[a,d]cycloheptene-7-carboxylic acid In other embodiments, the ratio (S)-enantiomer:(R)-enantiomer (w/w) is at least about 2:1 or about 5:1 or about 10:1 or about 20:1 or about 50:1.

In one embodiment, the composition comprises (S)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid and a physiologically acceptable carrier or excipient. In another embodiment, the composition is substantially free of (R)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid (contains at least about 98% or at least about 99% enantiomeric excess of (S)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid).

In another embodiment, the composition comprises (S)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid, (R)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a, d]cycloheptene-7-carboxylic acid and a physiologically acceptable carrier or excipient. In one embodiment, the composition comprises racemic-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid In other embodiments, the ratio (S)-enantiomer:(R)-enantiomer (w/w) is at least about 2:1 or about 5:1 or about 10:1 or about 20:1 or about 50:1.

Therapeutic Methods

The invention further relates to a method for treating (e.g., palliative, curative, prophylactic) a disease or disorder associated with pathogenic leukocyte recruitment, activation or recruitment and activation, mediated by chemokines or chemokine receptor function including chronic and acute inflammatory disorders.

As used herein "pathogenic leukocyte recruitment, activation or recruitment and activation" refers to leukocyte recruitment (e.g., accumulation of leukocytes at a sight of inflammation or injury) and/or activation (e.g., physiologic state in which leukocytes perform effector functions) that contributes to the conditions, processes or results of the disease or disorder to be treated. For example, in a subject afflicted with multiple sclerosis, recruitment and/or activation of T cells in the central nervous system is considered "pathogenic leukocyte recruitment, pathogenic leukocyte activation or pathogenic leukocyte recruitment and activation," because recruited and activated T cells contribute to the demyelination characteristic of that disease. Similarly, in a subject afflicted with rheumatoid arthritis, recruitment and/or activation of T cells in joints (e.g., synovial tissue or fluid) is considered "pathogenic leukocyte recruitment, pathogenic leukocyte activation or pathogenic leukocyte recruitment and activation," because recruited and activated T cells contribute to the tissue destruction characteristic of rheumatoid arthritis.

Diseases and disorders characterized by pathogenic leukocyte recruitment, pathogenic leukocyte activation or pathogenic leukocyte recruitment and activation that can be treated according to the methods described herein include, for example, acute and chronic inflammatory disorders characterized by the presence of CCL2 (MCP-1) CCL3 (MIP-1α), CCL4 (MIP-1β), CCL5 (RANTES), CCL7 (MCP-3), CCL8 (MCP-2), CCL13 (MCP-4), CCL14 (HCC-1), CCL15 (Lkn-1) and/or CCL23 (MPIF-1) responsive cells, such as T cells, monocytes or eosinophils. Such diseases or disorders include, but are not limited to, inflammatory arthritis (e.g., rheumatoid arthritis), inflammatory demyelinating disease (e.g., multiple sclerosis), atherosclerosis, arteriosclerosis, restenosis, ischemia/reperfusion injury, diabetes mellitus (e.g., type 1 diabetes mellitus), psoriasis, inflammatory bowel diseases such as ulcerative colitis and Crohn's disease, rejection (acute or chronic) of transplanted organs and tissues (e.g., acute allograft rejection, chronic allograft rejection), graft versus host disease, as well as allergies and asthma. Other diseases associated with aberrant leukocyte recruitment and/or activation which can be treated (including prophylactic treatments) with the methods disclosed herein are inflammatory diseases associated with viral (e.g., Human Immunodeficiency Virus (HIV)), bacterial or fungal infection, such as, AIDS associated encephalitis, AIDS related maculopapular skin eruption, AIDS related interstitial pneumonia, AIDS related enteropathy, AIDS related periportal hepatic inflammation and AIDS related glomerulo nephritis. The method comprises administering to the subject in need of treatment an effective amount of a compound (i.e., one or more compounds) described herein.

As used herein "inflammatory demyelinating disease" refers to acute and chronic inflammatory diseases characterized by demyelination of central nervous system tissue. The inflammatory demyelinating disease can be an acute inflammatory demyelinating disease, for example, acute disseminated encephalomyelitis, Guillain-Barre syndrome or acute hemorrhagic leukoencephalitis. In other embodiments, the inflammatory demyelinating disease can be a chronic inflammatory demyelinating disease, for example, multiple sclerosis, chronic inflammatory demyelinating polyradiculoneuropathy.

In a preferred embodiment, the invention provides a method of treating multiple sclerosis, comprising administering an effective amount of a compound of Formula (I), (Ia), (II) or (IIa) to a subject in need thereof. The manifestation of MS is variable and the clinical course of MS can be grouped into four categories: relapsing-remitting, primary progressive, secondary progressive and progressive-relapsing. The method of the invention can be used to treat MS which presents with each of the recognized clinical courses. Accordingly, a compound of the invention can be administered to a patient with a progressive course of MS to retard or prevent the progression of neurological impairment. A compound of the invention can also be administered to a subject with relapsing-remitting, secondary progressive or progressive-relapsing MS to inhibit relapse (e.g., an acute attack). For example, a compound of the invention can be administered to a subject with relapsing-remitting MS during the remitting phase of the disease to prevent or delay relapse.

As used herein, "inflammatory arthritis" refers to those diseases of joints where the immune system is causing or exacerbating inflammation in the joint, and includes rheumatoid arthritis, juvenile rheumatoid arthritis and spondyloarthropathies, such as ankylosing spondylitis, reactive arthritis, Reiter's syndrome, psoriatic arthritis, psoriatic spondylitis, enteropathic arthritis, enteropathic spondylitis, juvenile-onset spondyloarthropathy and undifferentiated spondyloarthropathy. Inflammatory arthritis is generally characterized by infiltration of the synovial tissue and/or synovial fluid by leukocytes.

In another preferred embodiment, the invention provides a method of treating rheumatoid arthritis, comprising administering an effective amount of a compound of Formula (I), (Ia), (II) or (IIa) to a subject in need thereof.

A "subject" is preferably a bird or mammal, such as a human (*Homo sapiens*), but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of a compound is an amount which inhibits binding of chemokine to receptor (e.g., CCR1) and thereby inhibits one or more processes mediated by the binding in a subject with a disease associated with pathogenic leukocyte recruitment, pathogenic leukocyte activation or pathogenic leukocyte recruitment and activation. Examples of such processes include leukocyte migration, integrin activation, transient increases in the concentration of intracellular free calcium $[Ca^{2+}]_i$ and granule release of proinflammatory mediators. An "effective amount" of a compound can achieve a desired therapeutic and/or prophylactic effect, such as an amount which results in the prevention of or a decrease in the symptoms associated with a disease associated with pathogenic leukocyte recruitment, pathogenic leukocyte activation or pathogenic leukocyte recruitment and activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. An antagonist of chemokine receptor function can also be administered in combination with one or more additional therapeutic agents, such as, theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNβ-1b)) and the like.

When a compound of the invention is administered in combination with another therapeutic agent, the compound and agent can be administered in a manner that afford overlap of pharmacological activity, for example, concurrently or sequentially.

The compound can be administered by any suitable route, including, for example, orally in capsules, suspensions or tablets or by parenteral administration. Parenteral administration can include, for example, systemic administration, such as by intramuscular, intravenous, subcutaneous or intraperitoneal injection. The compound can also be administered orally (e.g., dietary), transdermally, topically, by inhalation (e.g., intrabronchial, intranasal, oral inhalation or intranasal drops), or rectally, depending on the disease or condition to be treated. Oral or parenteral administration are preferred modes of administration. The compound can be administered to the individual as part of a pharmaceutical or physiological composition.

The activity of compounds of the present invention can be assessed using suitable assays, such as receptor binding assays or chemotaxis assays. For example, as described in the Examples, small molecule antagonists of MIP-1ÿ binding have been identified utilizing THP-1 cells membranes. Specifically, a high through-put receptor binding assay, which monitors $^{125}$I-MIP-1α binding to THP-1 cell membranes, was used to identify small molecule antagonists which block binding of MIP-1α. Compounds of the present invention can also be identified by virtue of their ability to inhibit the activation steps triggered by binding of a chemokine (e.g., CCL2 (MCP-1) CCL3 (MIP-1α), CCL4 (MIP-1β), CCL5 (RANTES), CCL7 (MCP-3), CCL8 (MCP-2), CCL13 (MCP-4), CCL14 (HCC-1), CCL15 (Lkn-1), CCL23 (MPIF-1)) to its receptor (CCR-1), such as chemotaxis, integrin activation and granule mediator release. They can also be identified by virtue of their ability to block chemokine (e.g., CCL2 (MCP-1) CCL3 (MIP-1α), CCL4 (MIP-1β), CCL5 (RANTES), CCL7 (MCP-3), CCL8 (MCP-2), CCL13 (MCP-4), CCL14 (HCC-1), CCL15 (Lkn-1), CCL23 (MPIF-1)) induced chemotaxis of, for example, HL-60 cells, T-cells, peripheral blood mononuclear cells or eosinophils.

EXAMPLES

Scheme 1

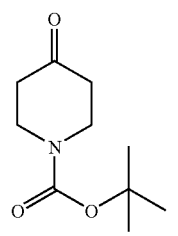

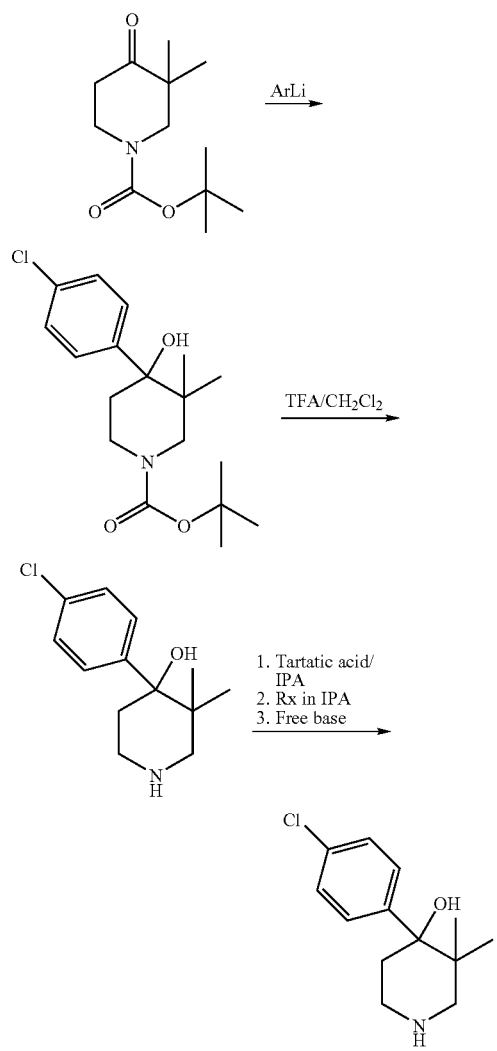

Scheme 2

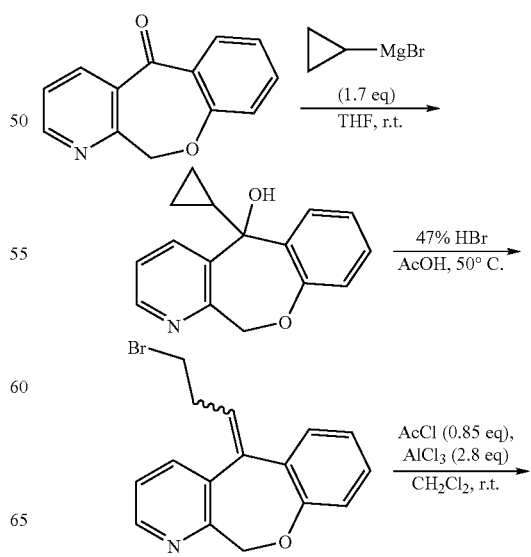

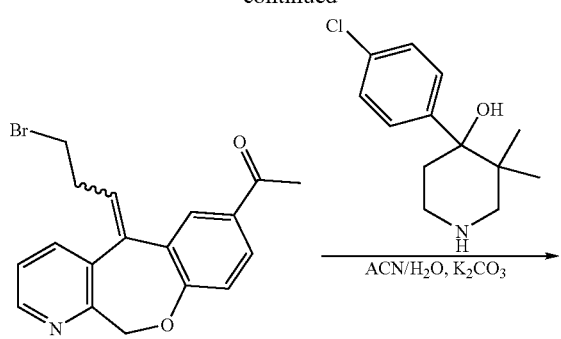

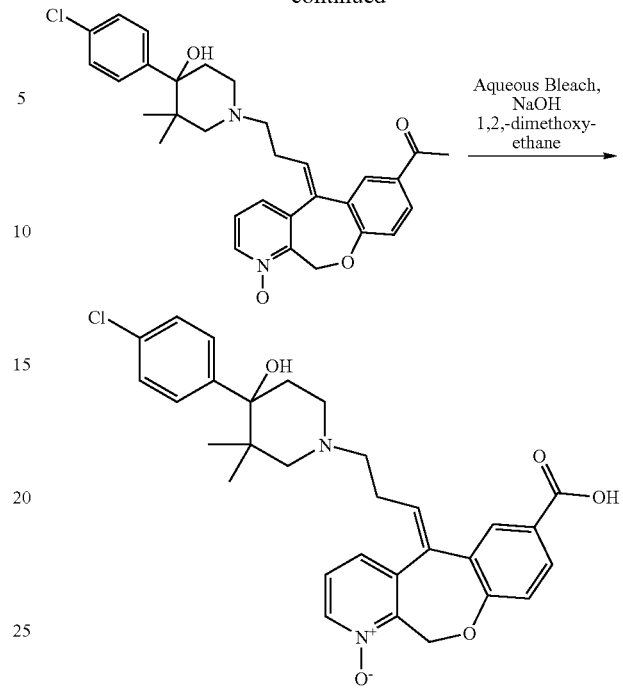

Example 1

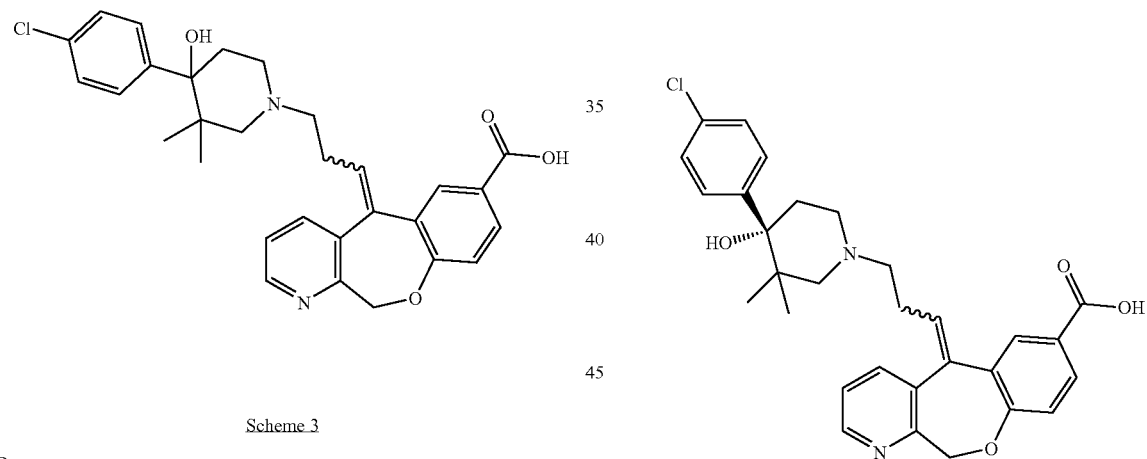

Scheme 3

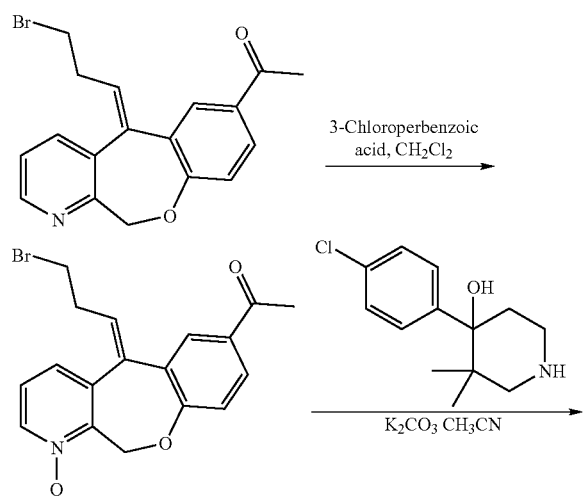

(S)-5-{3-[4-(4-Chloro-phenyl)-4-hydroxy-3,3-dimethyl-piperidin-1-yl]-propylidene}-5,11-dihydro-10-oxa-1-aza-dibenzo[a,d]cycloheptene-7-carboxylic acid Step 1: 3,3-Dimethyl-4-oxo-piperidine-1-carboxylic acid tert-butyl ester To a dry, 2 L 2-neck, round-bottom flask equipped with a magnetic stirrer, a condenser, and a large 10° C. water bath was added 4-oxo-piperidine-1-carboxylic acid tert-butyl ester (125 g, 628 mmol) and anhydrous tetrahydrofuran (1 L). To the resulting yellow solution was added methyl iodide (85 mL, 1365 mmol). Sodium t-butoxide (150 g, 1560 mmol) was then added portionwise over 30 minutes. An exotherm was detected, especially at the beginning of the addition. The reaction mixture did warm to a gentle reflux, the rate was controlled by the speed of addition of base. The mixture was stirred an additional 30 minutes. The solvent was removed in vacuo. The oily residue was treated with NH$_4$Cl/water (500 mL), and extracted with ether (3×200 mL). The combined organics were washed with brine, dried over Na$_2$SO$_4$, and filtered through a short plug of silica gel. The solvent was removed in vacuo, and the resulting yellow oil had started to crystallize. It was left under high vacuum overnight. The mixture was slurried in hexane (50-100 mL) and sonicated for one minute. The yellow solid was collected by filtration and washed with hexane (100 mL). The first crop of 3,3-dimethyl-4-oxo-piperidine-1-carboxylic acid tert-butyl ester yielded a yellow solid. (See, preparation of (37) in Vice, S. et al., *J. Org. Chem.*, 66:2487-2492 (2001).)

$^1$H-NMR (CDCl$_3$, 300 MHz) δ: 1.13 (s, 6 H), 1.49 (s, 9 H), 2.49 (t, 2 H), 3.43 (br s, 2H), 3.73 (t, 2 H).

Step 2: 4-(4-Chloro-phenyl)-4-hydroxy-3,3-dimethyl-piperidine-1-carboxylic acid tert-butyl ester A 2-neck, 2-L round bottom flask was fitted with two 125 mL dropping funnels and a stir bar. The assembly was flame-dried under dry nitrogen. The flask was charged with THF (700 mL) and 4-bromo-chlorobenzene (33.7 g, 176 mmol, 2.5 eq.). The resulting solution was cooled to −78° C. in a dry ice/acetone bath. To one of the dropping funnels was added butyllithium (2.5 M in hexanes, 70 mL, 175 mmol, 2.5 eq) via canula. The butyllithium solution was slowly added to the cold THF solution over 1 hour. Stirring continued for an additional 0.5 hour affording a white suspension. A solution of 3,3-dimethyl-4-oxo-piperidine-1-carboxylic acid tert-butyl ester (16.0 g, 70.5 mmol, 1 eq.) in THF (100 mL) was prepared and added to the reaction mixture via the second dropping funnel over 1.75 hours. The resulting mixture was stirred at −78° C. for 2 hours, at which time the reaction appeared to be essentially complete by TLC analysis. Saturated aqueous NH$_4$Cl (150 mL) was added and the reaction was allowed to warm to room temperature. Water (150 mL) was added and the mixture was extracted with ethyl acetate (2+1 L). The combined extracts were washed with water and brine, dried over magnesium sulfate, filtered and concentrated. The solid residue was triturated with ethyl acetate and filtered. The supernatant was concentrated and triturated with ether. The resulting supernatant was then triturated with ether/petroleum ether. The resulting solids were combined to afford 4-(4-Chloro-phenyl)-4-hydroxy-3,3-dimethyl-piperidine-1-carboxylic acid tert-butyl ester as an off-white solid.

$^1$H-NMR (CDCl$_3$, 300 MHz) δ: 0.82 (s, 6 H), 1.34-1.44 (m, 2 H), 1.49 (s, 9 H), 2.67 (ddd, 1 H), 3.10-3.70 (m, 3 H), 4.00-4.30 (m, 1H), 7.31 (d, 2 H), 7.39 (d, 2 H).

Step 3: 4-(4-Chloro-phenyl)-3,3-dimethyl-piperidin-4-ol

To a cooled (0° C.) solution of 4-(4-Chloro-phenyl)-4-hydroxy-3,3-dimethyl-piperidine-1-carboxylic acid tert-butyl ester (10.42 g, 30.7 mmol) in methylene chloride (300 mL) was slowly added trifluoroacetic acid (60 mL) over 1.25 hours. The resulting yellow solution was stirred at 0° C. for an additional 1.5 hours. The mixture was concentrated under reduced pressure and the residue dissolved in ethyl acetate (1.2 L), and washed with aqueous sodium hydroxide (1 N, 150 mL). The aqueous layer was extracted with additional ethyl acetate (200 mL) and the combined extracts were washed with brine, dried over sodium sulfate, filtered and concentrated. The resulting solid residue was triturated with ether to afford 4-(4-Chloro-phenyl)-3,3-dimethyl-piperidin-4-ol as an off-white solid.

$^1$H-NMR (CD$_3$OD, 300 MHz) δ: 0.73 (s, 3 H), 0.85 (s, 3 H), 1.42 (ddd, 1 H), 2.36 (d, 1H), 2.61 (ddd, 1 H), 2.91 (br dd, 1 H), 3.08-3.19 (m, 2 H), 7.26-7.32 (m, 2 H), 7.44-7.50 (m, 2 H).

MS m/z: 240 (M+1).

Step 4: (S)-4-(4-chloro-phenyl)-3,3-dimethyl-piperidin-4-ol

A visibly clean 5 L, 3-neck flask was fitted with an overhead stirrer and flushed with nitrogen for 20 min. Racemic 4-(4-Chloro-phenyl)-3,3-dimethyl-piperidin-4-ol (202 g, 843 mmol), L-(+)-tartaric acid (114 g, 759 mmol) and 4040 mL of a 9:1 butanone:water mixture were added to the flask. The mixture was heated to reflux. Water (202 mL) was added portionwise over 45 min (ratio of butanone to water: 6:1) to fully dissolve the solid mixture. Reflux was continued an additional 45 minutes, the heat source was then turned off and the flask allowed to cool slowly to room temperature overnight. Solids were removed under suction filtration and dried for about 3 days in vacuo to afford S-enantiomer as the L-(+) tartrate salt, which was partitioned between 1 M NaOH and methylene chloride (brine washed and sodium sulfate-dried) to afford the free base.

$^1$H-NMR (CD$_3$OD, 300 MHz) δ: 0.73 (s, 3 H), 0.85 (s, 3 H), 1.42 (ddd, 1 H), 2.36 (d, 1H), 2.61 (ddd, 1 H), 2.91 (br dd, 1 H), 3.08-3.19 (m, 2 H), 7.26-7.32 (m, 2 H), 7.44-7.50 (m, 2 H).

MS m/z: 240 (M+1).

Step 5: 5-Cyclopropyl-5,11-dihydro[1]benzoxepino[2,3-b]pyridin-5-ol

A dry 2 L three-necked, round-bottomed flask was fitted with a magnetic stirring bar, a glass stopper, a rubber septum, and an argon inlet. Under an argon atmosphere, 50.0 g. of 5,11-dihydro[1]benzoxepino[3,4-b]pyridine-5-one (prepared by the method of Inoue et al., *Synthesis* 1:113-116 (1997), (0.24 mole)) and 500 mL of dry tetrahydrofuran were added to the flask and the flask was cooled with an ice bath. A freshly prepared cyclopropylmagnesium bromide tetrahydrofuran solution (50.0 g. of cyclopropylmagnesium bromide was prepared from cyclopropylbromide (0.41 mole) and 12.0 g. of magnesium turnings (0.49 mole) in 400 mL of dry tetrahydrofuran) was introduced by needle over a period of 5 minutes. The ice bath was removed, and the mixture was stirred for 30 minutes. The reaction mixture was slowly poured into 500 mL of saturated ammonium chloride solution, the mixture was extracted with two 300 mL portions of ethyl acetate, and the combined organic extracts are washed with 300 mL of saturated aqueous sodium chloride. The organic solution was dried with anhydrous magnesium sulfate, filtered, and evaporated (aspirator vacuum, ca. 30° C.). To the residual solid was added 150 mL of a 1:1 (v/v) hexane-ethyl acetate mixture, and the mixture was sonicated for 15 minutes, filtered and washed with a 1:1 (v/v) hexane-ethyl acetate mixture to yield the titled compound as a pale yellow solid.

Step 6: 5-(3-Bromopropylidene)-5,11-dihydro[1]benzoxepino[2,3-b]pyridine

To a 2 L eggplant flask with a magnetic stirring bar was added 75.0 g. of 5-Cyclopropyl-5,11-dihydro[1]benzoxepino [2,3-b]pyridin-5-ol (0.30 mole) and 75 mL of acetic acid. The solution was cooled with water (ca. 10° C.), 120 ml of 47% aqueous hydrobromic acid was added over a period of 5 minutes. The reaction mixture was warmed to 60° C., stirred for an hour, and evaporated (aspirator vacuum, ca. 50° C.) to ca. 200 mL. The reaction mixture was poured to 1500 mL of saturated aqueous sodium bicarbonate, the mixture is extracted with two 800 mL portions of ethyl acetate, and the combined organic extracts are washed with 500 mL of saturated aqueous sodium chloride. The organic solution was dried with anhydrous magnesium sulfate, filtered, and evaporated (aspirator vacuum, ca. 30° C.). The oily residue was chromatographed on 500 g. of Silica gel 60 by eluting with 5:1-4:1 (v/v) hexane-ethyl acetate mixture. The elution was evaporated, giving the titled compound as a pale yellow oil.

Step 7: 7-Acetyl-5-(3-bromopropylidene)-5,11-dihydro[1]benzoxepino[2,3-b]pyridine A dry 3 L three-necked, round-bottomed flask was fitted with a magnetic stirring bar, a glass stopper, a rubber septum, and an argon inlet. Under an argon atmosphere, 94.0 g. of 5-(3-Bromopropylidene)-5,11-dihydro[1]benzoxepino[2,3-b]pyridine (0.30 mole) and 900 mL of dry dichloromethane were added to the flask and the flask was cooled with an ice bath. To the solution was slowly added 78.5 g. of aluminum chloride (0.83 mole), followed by 17.8 mL of acetyl chloride (0.25 mole), and the mixture was stirred for an hour at 0° C. The reaction mixture was poured to 1500 g of ice, and the layers were separated. The aqueous layer was extracted with three 400 mL portions of ethyl acetate. Dichloromethane layer and the organic extracts were combined and washed successively with 1 μL of saturated aqueous sodium bicarbonate and 1 L of saturated aqueous sodium chloride. The organic solution was dried with anhydrous magnesium sulfate, filtered, and evaporated (aspirator vacuum, ca. 30° C.). The oily residue was chromatographed on 800 g. of Silica gel 60 by eluting with 5:1-1:1 (v/v) hexane-ethyl acetate mixture. The elution was evaporated, giving the titled compound as a pale yellow solid.

Step 8: (S)-1-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yl)-ethanone To a suspension of the (S)-4-(4-chloro-phenyl)-3,3-dimethyl-piperidin-4-ol (5.50 g, 22.94 mmol) in acetonitrile (200 mL) and water (50 mL) was added potassium carbonate (7.17 g, 51.9 mmol) followed by solid 1-[5-(3-bromo-propylidene)-5,11-dihydro-10-oxa-1-aza-dibenzo[a,d]cyclohepten-7-yl]-ethanone (6.30 g, 17.3 mmol). The heterogeneous mixture was stirred at room temperature 4 hours, warmed to 50° C. and stirred 13 hours. The mixture was cooled to room temperature and acetonitrile was removed under reduced pressure. The aqueous layer was extracted with ethyl acetate (750 mL) and the extract was washed with brine, dried over sodium sulfate, filtered and concentrated. The crude residue was purified by silica gel chromatography (3:1 ethyl acetate: hexanes) to afford (S)-1-(5-{3-[4-(4-Chloro-phenyl)-4-hydroxy-3, 3-dimethyl-piperidin-1-yl]-propylidene}-5,11-dihydro-10-oxa-1-aza-dibenzo[a,d]cyclohepten-7-yl)-ethanone as an off-white solid.

$^1$H-NMR (CDCl$_3$) δ: 0.6-0.9 (6H, d), 1.2-1.6 (4H, m), 2.2-2.4 (4H, m), 2.55 (3H, s), 2.8 (2H, d), 5.3 (2H, brs), 6.25 (1H, t), 6.85 (1H, d), 7.27-7.4 (6H, m), 7.6-7.8 (2H, m), 8.0 (1H, d), 8.5 (1H, d).

MS m/z: 517 (M+1).

Step 9

The product of step 8 (500 mg, 0.969 mmol), NaOH (2M in water, 4.84 mmol, 2.42 mL), sodium hypochlorite (4% available chlorine, 3.6 mmol) and DME (10 vols, 5 mL) were charged to a 25 mL round bottom flask and stirred at room temperature overnight. After 12 hours, sodium bisulfite (5 mL, saturated aq solution) was added and the reaction extracted with ethyl acetate (4×5 mL); the organic layers were combined and dried over sodium sulfate, filtered and evaporated under reduced pressure to yield 500 mg (96% yield) of a yellow solid. The solid was dissolved in water (20 vols, 10 mL) and acidified with acetic acid to pH 6.15. Upon acidification, a cream-colored solid was precipitated; the solid was filtered and placed in a vacuum oven for about two days to afford the titled compound.

$^1$H-NMR (CD$_3$OD) δ: 0.75 (s, 3 H), 0.86 (s, 3 H), 1.63 (d, 1 H), 2.49-2.66 (m, 2 H), 2.70-2.89 (m, 2 H), 2.99-3.23 (m, 5 H), 5.10-5.50 (brs, 2 H), 6.15 (t, 1 H), 6.75 (d, 2 H), 7.25-7.31 (m, 2 H), 7.39-7.47 (m, 2 H), 7.71-7.81 (m, 2 H), 7.98 (d, 1 H), 8.45 (d, 1 H).

MS m/z: 519 (M+1).

Example 2

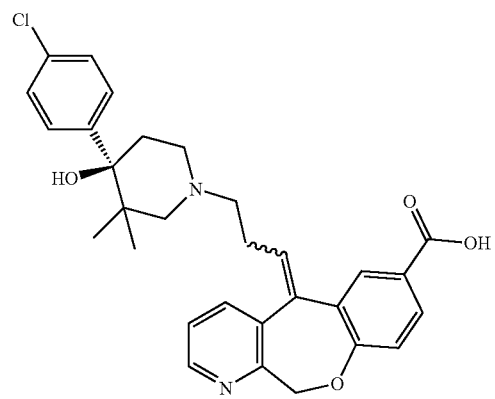

(R)-5-{3-[4-(4-Chloro-phenyl)-4-hydroxy-3,3-dimethyl-piperidin-1-yl]-propylidene}-5, 11-dihydro-10-oxa-1-aza-dibenzo[a,d]cycloheptene-7-carboxylic acid Part 1: (R)-4-(4-chloro-phenyl)-3,3-dimethyl-piperidin-4-ol Racemic 4-(4-chloro-phenyl)-3,3-dimethyl-piperidin-4-ol (0.500 g, 2.086 mmol) was dissolved in minimal hot isopropyl alcohol (ca. 5 mL). The hot solution was filtered through a plug of cotton and transferred to a solution of (1S)-(+)-10-camphorsulfonic acid (0.484 g, 2.086 mmol) in isopropyl alcohol (ca. 3 mL). The mixture was stirred vigorously for several minutes, during which a thick precipitate formed, and allowed to cool to room temperature over 0.25 hour. The solids were removed by suction filtration and dried in vacuo. The dried salt was dissolved in hot isopropyl alcohol (ca. 50 mL), filtered through a cotton plug, and allowed to slowly cool to room temperature, undisturbed, overnight. The solids that formed on cooling (95 mg, 19% of theoretical) were removed by suction filtration and shown by analytical HPLC to be enantiomerically pure. The salt was suspended in ethyl acetate and neutralized with sodium hydroxide (1 N). The homogenous organic phase was washed with water and brine, dried over sodium sulfate, filtered and dried to afford R-4-(4-chloro-phenyl)-3,3-dimethyl-piperidin-4-ol.

$^1$H-NMR (CD$_3$OD, 300 MHz) δ: 0.73 (s, 3 H), 0.85 (s, 3 H), 1.42 (ddd, 1 H), 2.36 (d, 1 H), 2.61 (ddd, 1 H), 2.91 (br dd, 1 H), 3.08-3.19 (m, 2 H), 7.26-7.32 (m, 2H), 7.44-7.50 (m, 2 H).

MS m/z: 240 (M+1).

Part 2

The compound was prepared essentially as described in Steps 5-9 of Example 1, but replacing (5)-4-(4-chloro-phenyl)-3,3-dimethyl-piperidin-4-ol with (R)-4-(4-chloro-phenyl)-3,3-dimethyl-piperidin-4-ol.

Example 3

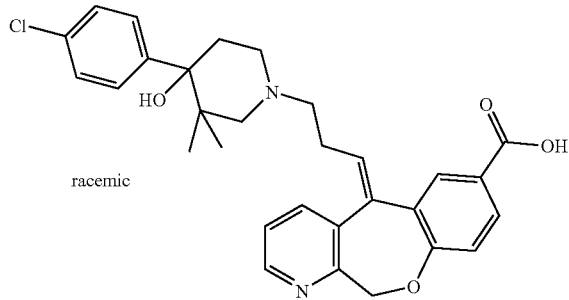

racemic-5-{3-[4-(4-Chloro-phenyl)-4-hydroxy-3,3-dimethyl-piperidin-1-yl]-propyliden e}-5,11-dihydro-10-oxa-1-aza-dibenzo[a,d]cycloheptene-7-carboxylic acid The racemic material was prepared essentially as described in Steps 5-9 of Example 1, but replacing (5)-4-(4-chlorophenyl)-3,3-dimethyl-piperidin-4-ol with racemic 4-(4-chloro-phenyl)-3,3-dimethyl-piperidin-4-ol.

Example 4

THP-1 Cell Membrane Preparation and Binding Assay

Membranes were prepared from THP-1 cells (ATCC. #TIB202). Cells were harvested by centrifugation, washed twice with PBS (phosphate-buffered saline), and the cell pellets were frozen at −70 to −85° C. The frozen pellet was thawed in ice-cold lysis buffer consisting of 5 mM HEPES (N-2-hydroxyethylpiperazine-N'-2-ethane-sulfonic acid) pH 7.5, 2 mM EDTA (ethylenediaminetetraacetic acid), 5 μg/ml each aprotinin, leupeptin, and chymostatin (protease inhibitors), and 100 μg/ml PMSF (phenyl methane sulfonyl fluoride—also a protease inhibitor), at a concentration of 1 to $5 \times 10^7$ cells/ml. This procedure results in cell lysis. The suspension was mixed well to resuspend all of the frozen cell pellet. Nuclei and cell debris were removed by centrifugation of 400×g for 10 minutes at 4° C. The supernatant was transferred to a fresh tube and the membrane fragments were collected by centrifugation at 25,000×g for 30 minutes at 4° C. The supernatant was aspirated and the pellet was resuspended in freezing buffer consisting of 10 mM HEPES pH 7.5, 300 mM sucrose, 1 μg/ml each aprotinin, leupeptin, and chymostatin, and 10 μg/ml PMSF (approximately 0.1 ml per each $10^8$ cells). All clumps were resolved using a minihomogenizer, and the total protein concentration was determined using a protein assay kit (Bio-Rad, Hercules, Calif., cat #500-0002). The membrane solution was then aliquoted and frozen at −70 to −85° C. until needed.

Binding Assays utilized the membranes described above. Membrane protein (2 to 20 μg total membrane protein) was incubated with 0.1 to 0.2 nM 125I-labeled MIP-1α with or without unlabeled competitor (MIP-1ÿ) or various concentrations of compounds. The binding reactions were performed in 60 to 100 μl of a binding buffer consisting of 10 mM HEPES pH 7.2, 1 mM CaCl2, 5 mM MgCl2, and 0.5% BSA (bovine serum albumin), for 60 min at room temperature. The binding reactions were terminated by harvesting the membranes by rapid filtration through glass fiber filters (GF/B or GF/C, Packard) which were presoaked in 0.3% polyethyleneimine. The filters were rinsed with approximately 600 μl of binding buffer containing 0.5 M NaCl, dried, and the amount of bound radioactivity was determined by scintillation counting. The activities of test compounds are reported in the Table.

Example 5

In Vivo Efficacy Model

An animal model of neutrophil recruitment in response to MIP-1α was used to evaluate the biological/pharmacodynamic activity of the compounds. Compounds were administered to female Hartley guinea pigs orally (doses ranged from about 0.5 mg/kg to about 5.0 mg/kg) 30 minutes prior to intradermal injections of murine MIP-1α (100 pmol/site) or phosphate buffered saline (PBS). Skin punch biopsies were taken 5 hours later and processed for myeloperoxidase (MPO) measurements. MPO activity was used as an indicator for neutrophil recruitment to the injection site. The results are presented in the Table.

Example 6

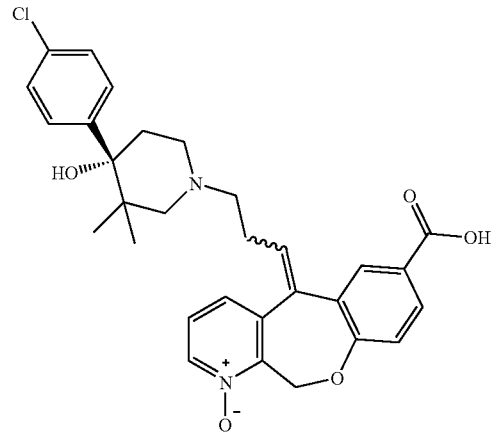

(S)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid Example 7

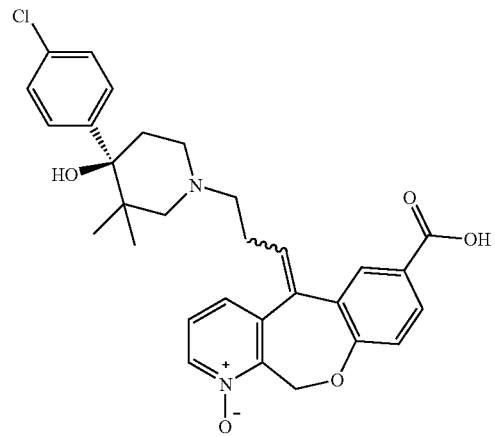

(R)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid Example 8

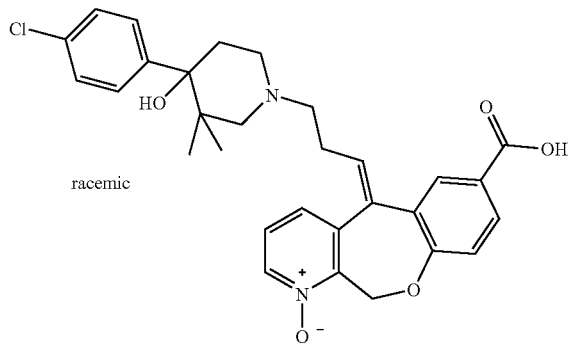

racemic racemic-5-{3-[4-(4-Chloro-phenyl)-4-hydroxy-3,3-dimethyl-piperidin-1-yl]-propyliden e}-1-oxy-5,11-dihydro-10-oxa-1-aza-dibenzo[a,d]cycloheptene-7-carboxylic acid Reference Example

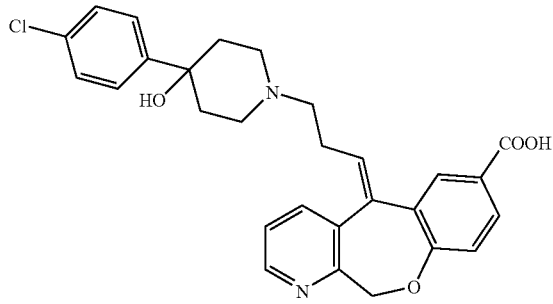

The Reference Example was prepared as described in WO 01/09138.

TABLE

| Example | Inhibition of $^{125}$I-MIP-1α Binding to THP-1 Cell Membranes (Ki (nM)) | Efficacy: Guinea Pig Neutrophil Recruitment (ED50 (mg/kg)) |
| --- | --- | --- |
| 1 | 2.3 | 0.12 |
| 2 | >1000 | not determined |
| 3 | 3 | 99% inhibition at 2.5 mg/kg |
| Reference Example | 7.8 | 3.6 |

The data presented in the Table demonstrate that Examples 1 and 3 have greater oral bioavailability and efficacy in comparison to the structurally related compound of the Reference Example. Examples 1 and 3 also showed greater selectivity, compared to structurally related compounds, when assayed on other G protein-coupled receptors and ion channels.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising (S)-5-{3-[4-(4-Chloro-phenyl)-4-hydroxy-3,3-dimethyl-piperidin-1-yl]-propylidene}-5,11-dihydro-10-oxa-1-aza- dibenzo[a,d]cycloheptene-7-carboxylic acid or physiologically acceptable salt thereof, (R)-5-{3-[4-(4-Chloro-phenyl)-4-hydroxy-3,3-dimethyl-piperidin-1-yl]-propylidene}-5,11-dihydro-10-oxa-1-aza-dibenzo[a,d]cycloheptene-7-carboxylic acid or physiologically acceptable salt thereof, and a physiologically acceptable carrier or excipient, wherein the ratio of (S)-enantiomer to (R)-enantiomer is at least about 2:1.

2. The pharmaceutical composition of claim 1 wherein the ratio of (S)-enantiomer to (R)-enantiomer is at least about 5:1.

3. The pharmaceutical composition of claim 1 wherein the ratio of (S)-enantiomer to (R)-enantiomer is at least about 10:1.

4. The pharmaceutical composition of claim 1 wherein the ratio of (S)-enantiomer to (R)-enantiomer is at least about 20:1.

5. The pharmaceutical composition of claim 1 wherein the ratio of (S)-enantiomer to (R)-enantiomer is at least about 50:1.

6. The pharmaceutical composition of claim 1, wherein said pharmaceutical composition is substantially free of (R)-5-{3-[4-(4-Chloro-phenyl)-4-hydroxy-3,3-dimethyl-piperidin-1-yl]-propylidene}-5,11-dihydro-10-oxa-1-aza-dibenzo[a,d]cycloheptene-7-carboxylic acid and physiologically acceptable salts thereof.

7. The pharmaceutical composition of claim 1, wherein said pharmaceutical composition contains at least about 98% enantiomeric excess of (S)-5-{3-[4-(4-Chloro- phenyl)-4-hydroxy-3,3-dimethyl-piperidin-1-yl]-propylidene}-5,11-dihydro-10-oxa-1-aza-dibenzo[a,d]cycloheptene-7-carboxylic acid) and physiologically acceptable salts thereof.

8. The pharmaceutical composition of claim 1, wherein said pharmaceutical composition contains at least about 99% enantiomeric excess of (S)-5-{3-[4-(4-Chloro- phenyl)-4-hydroxy-3,3-dimethyl-piperidin-1-yl]-propylidene}-5,11-dihydro-10-oxa-1-aza-dibenzo[a,d]cycloheptene-7-carboxylic acid) and physiologically acceptable salts thereof.

9. A pharmaceutical composition comprising (S)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid or physiologically acceptable salt thereof, (R)-5-{3-[4(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid or physiologically acceptable salt thereof, and a physiologically acceptable carrier or excipient, wherein the ratio of (S)-enantiomer to (R)-enantiomer is at least about 2:1.

10. The pharmaceutical composition of claim 9 wherein the ratio of (S)-enantiomer to (R)-enantiomer is at least about 5:1.

11. The pharmaceutical composition of claim 9 wherein the ratio of (S)-enantiomer to (R)-enantiomer is at least about 10:1.

12. The pharmaceutical composition of claim 9 wherein the ratio of (S)-enantiomer to (R)-enantiomer is at least about 20:1.

13. The pharmaceutical composition of claim 9 wherein the ratio of (S)-enantiomer to (R)-enantiomer is at least about 50:1.

14. The pharmaceutical composition of claim 9, wherein said pharmaceutical composition is substantially free of (R)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid and physiologically acceptable salts thereof.

15. The pharmaceutical composition of claim 9, wherein said pharmaceutical composition contains at least about 98% enantiomeric excess of (S)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid and physiologically acceptable salts thereof.

16. The pharmaceutical composition of claim 9, wherein said pharmaceutical composition contains at least about 99% enantiomeric excess of ((S)-5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cycloheptene-7-carboxylic acid and physiologically acceptable salts thereof.

* * * * *

UNITED STATES PATENT AND TRADEMARK OFFICE
CERTIFICATE OF CORRECTION

| | | |
|---|---|---|
| PATENT NO. | : 7,977,350 B2 | Page 1 of 1 |
| APPLICATION NO. | : 12/765070 | |
| DATED | : July 12, 2011 | |
| INVENTOR(S) | : Carson et al. | |

It is certified that error appears in the above-identified patent and that said Letters Patent is hereby corrected as shown below:

On title page

In the Related U.S. Application Data in Field (63) on page 1, after "Pat. No. 7,732,458" please insert:

--, which is a continuation of U.S. Patent Application No. 11/204,930, filed August 16, 2005, which is a continuation of U.S. Patent Application No. 10/706,835, filed November 12, 2003, which claims the benefit of U.S. Provisional Application No. 60/425,947, filed November 13, 2002--

Signed and Sealed this
Twenty-seventh Day of September, 2011

David J. Kappos
*Director of the United States Patent and Trademark Office*